United States Patent [19]
Treatch

[11] Patent Number: 4,830,018
[45] Date of Patent: May 16, 1989

[54] SYSTEM FOR AMBULATORY BLOOD PRESSURE MONITORING
[75] Inventor: James E. Treatch, Phoenix, Ariz.
[73] Assignee: Pulse Trend, Inc., Phoenix, Ariz.
[21] Appl. No.: 98,550
[22] Filed: Sep. 21, 1987
[51] Int. Cl.4 .............................................. A61B 5/02
[52] U.S. Cl. ..................................... 128/677; 128/904
[58] Field of Search ............... 128/672, 677, 680–683, 128/687–688, 689–690, 904, 670–671, 700, 706–707, 684, 14 686

[56] References Cited
U.S. PATENT DOCUMENTS

| | | | |
|---|---|---|---|
| 4,068,096 | 1/1978 | Rattenborg et al. | |
| 4,151,831 | 5/1979 | Lester | 128/738 X |
| 4,185,621 | 1/1980 | Morrow | 128/672 |
| 4,216,462 | 8/1980 | McGrath et al. | 128/904 X |
| 4,224,948 | 9/1980 | Cramer et al. | 128/690 |
| 4,252,127 | 2/1981 | Gemelke | 128/680 |
| 4,281,663 | 8/1981 | Pringle | 128/689 |
| 4,305,401 | 12/1981 | Reismueller et al. | 128/690 |
| 4,326,537 | 4/1982 | Croslin | 128/687 |
| 4,378,807 | 4/1983 | Peterson et al. | 128/682 X |
| 4,404,974 | 9/1983 | Titus | 128/672 X |
| 4,407,295 | 10/1983 | Steuer et al. | 128/671 X |
| 4,469,107 | 9/1984 | Asmar et al. | 128/690 X |
| 4,592,018 | 5/1986 | Wiegman | 128/672 X |
| 4,608,994 | 9/1986 | Ozawa et al. | 128/670 |
| 4,622,979 | 11/1986 | Katchis et al. | 128/904 X |
| 4,660,567 | 4/1987 | Kaneko et al. | 128/680 X |

FOREIGN PATENT DOCUMENTS
0653845 1/1986 Switzerland ...................... 128/690
86/06603 11/1986 World Int. Prop. O. ............ 128/68

OTHER PUBLICATIONS
Fiegel; "Portable Blood Pressure Monitor", *IBM Technical Disclosure Bulletin*, vol. 9, No. 6, 11–1966.

Primary Examiner—Kyle L. Howell
Assistant Examiner—Angela D. Sykes
Attorney, Agent, or Firm—Kinney & Lange

[57] ABSTRACT

A system for acquiring, storing, transmitting and processing blood pressure information. The system utilizes an ambulatory patient unit which emits a warning signal alerting the patient that a blood pressure reading is about to be taken. The patient unit takes the blood pressure reading, by electronically manipulating a pressure cuff, and stores the blood pressure information in a memory device. After accumulating a plurality of blood pressure readings within the memory device, the patient unit is electrically coupled to a programmable control unit. The programmable control unit accesses the memory device within the patient unit and relays the blood pressure information to a central processing computer. A central processing computer generates medical reports based on blood pressure information received from various programmable control units.

7 Claims, 3 Drawing Sheets

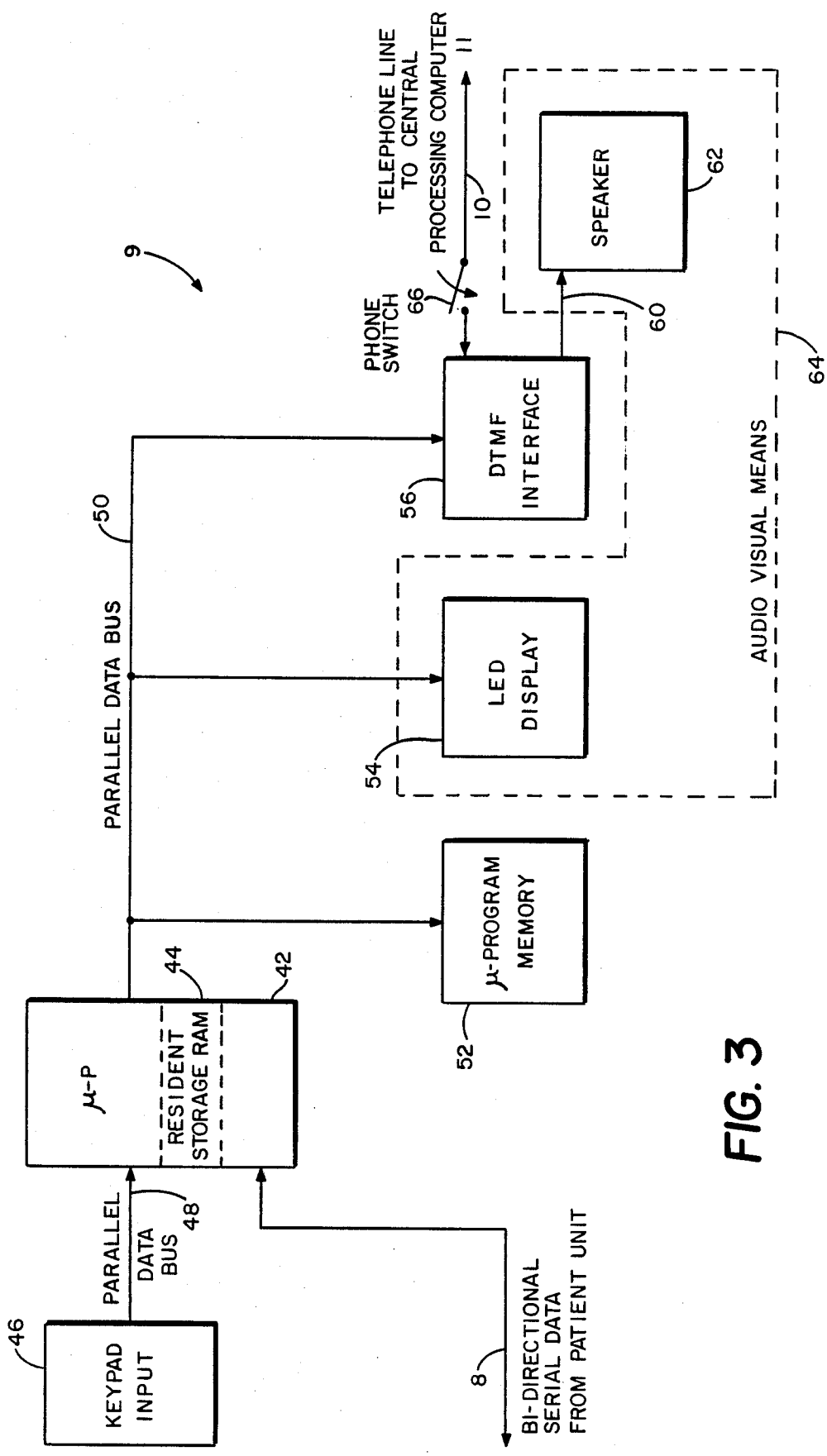

SYSTEM FOR AMBULATORY BLOOD PRESSURE MONITORING

BACKGROUND OF THE INVENTION

1. Field of the Invention

This invention relates to data acquisition systems. More particularly, it relates to systems for acquiring and manipulating blood pressure information taken from a plurality of patients.

2. Description of the Prior Art

There are 60 million hypertensives in the United States, 40 million of whom have been diagnosed. 30 million of those diagnosed are being treated by physicians. It is desirable for physicians who are treating hypertensives to monitor their patient's blood pressure throughout the day, on a day-to-day basis.

Existing blood pressure monitors are very expensive microprocessor based products. They are generally very intelligent, employing complex algorithms to not only take blood pressure readings, but to perform some sort of special analysis. Due to the complexity and expense of these monitors, it is hard for doctors to accumulate accurate, ambulatory hypertension monitoring information without a large investment.

SUMMARY OF THE INVENTION

The present invention is a system, which may be accessed by physicians at low cost, for acquiring, storing, transmitting and processing substantially error free blood pressure information. The system utilizes an inexpensive, microprocessor based, ambulatory patient unit. The patient unit emits a warning signal which alerts the patient that a blood pressure reading is about to be taken, then manipulates a pressure cuff and records the patient's blood pressure reading. The patient unit then stores the patient's blood pressure reading in resident memory.

After the desired number of blood pressure readings are taken, the patient unit is electronically coupled to an inexpensive microprocessor based programmable control unit which is located in the treating physician's office. The programmable control unit allows the physician to program the patient unit for a new test regimen. The programmable control unit also reads information contained in the memory within the patient unit and relays that information to a central processing computer.

The central processing computer communicates with a plurality of programmable control units over telephone lines. It receives and processes the blood pressure readings from all of these programmable control units and generates comprehensive medical reports based on that information.

The physician, then, can exercise ambulatory blood pressure monitoring techniques after purchasing only an inexpensive programmable control unit. Additionally, the centralized cost of one computer, which does all the analysis, is spread among many physicians. This is much less expensive to the physicians than requiring them to buy their own intelligent monitors for gathering information and doing analysis.

Another benefit of the central processing computer is that it collects a larger amount of blood pressure information than a physician's individual monitor. For this reason, a given patient's blood pressure information can be compared against that of a peer group. Therefore, the medical reports generated by a central processing computer are more comprehensive than those generated by an individual physician's blood pressure monitor.

BRIEF DESCRIPTION OF THE DRAWINGS

FIG. 3 is a more detailed block diagram of the control unit.

DETAILED DESCRIPTION OF THE PREFERRED EMBODIMENTS

Figure 1:
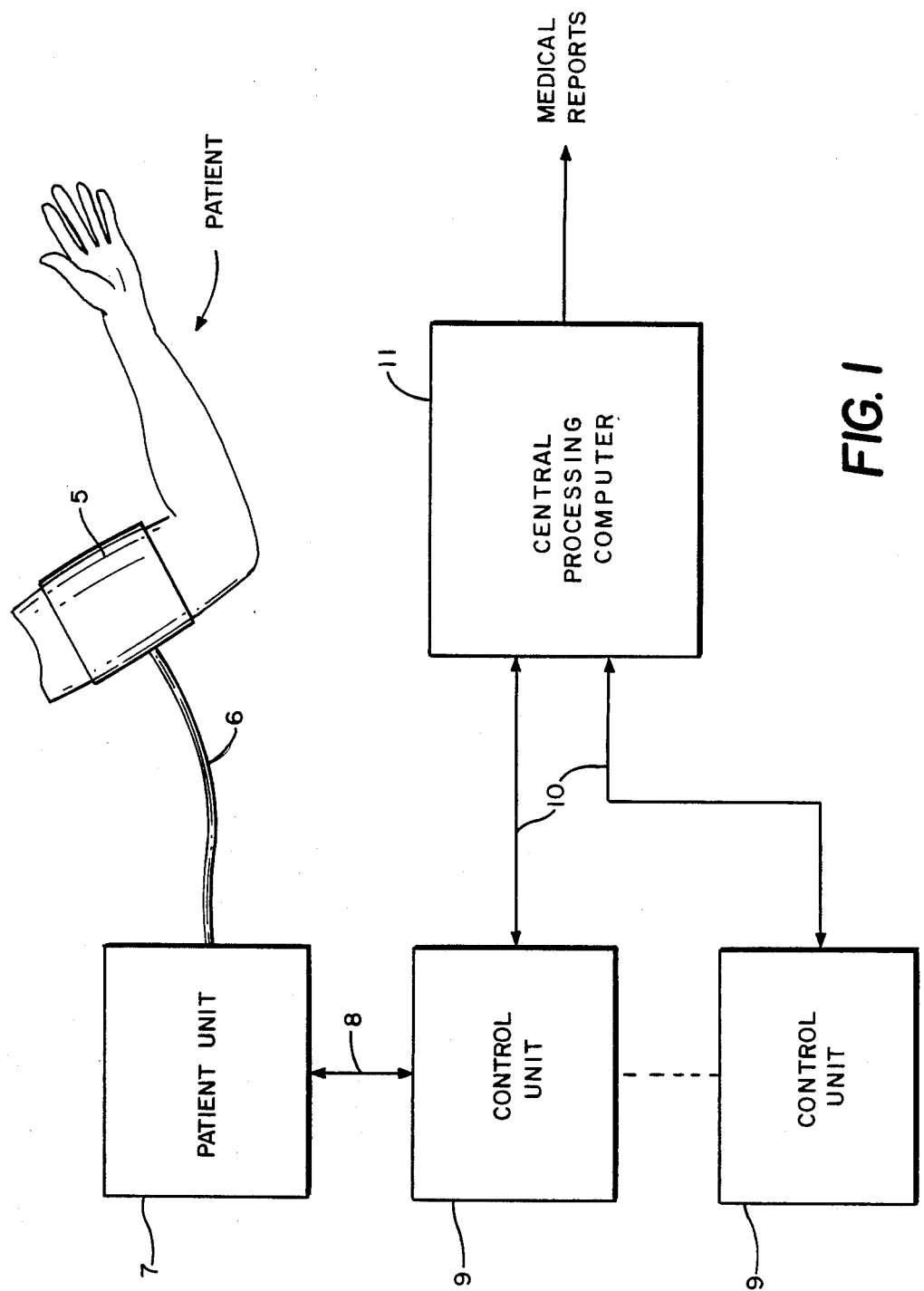
FIG. 1 is an overall block diagram of the blood pressure information acquisition and processing system.

In FIG. 1, an overall system block diagram is shown. A cuff 5, which is placed around a patient's arm and inflated to detect blood pressure, is shown attached to an umbilical cord 6. A patient unit 7 receives blood pressure reading signals from cuff 5 via umbilical cord 6. As shown, patient unit 7 is detachably linked through a bi-directional serial data link 8 to control unit 9. In accordance with this invention, a plurality of control units 9, which are located in physician's offices, are linked via telephone lines 10 to central processing computer 11. Central processing computer 11 accummulates and analyzes data received from control units 9, and generates medical reports based on that information.

Figure 2:
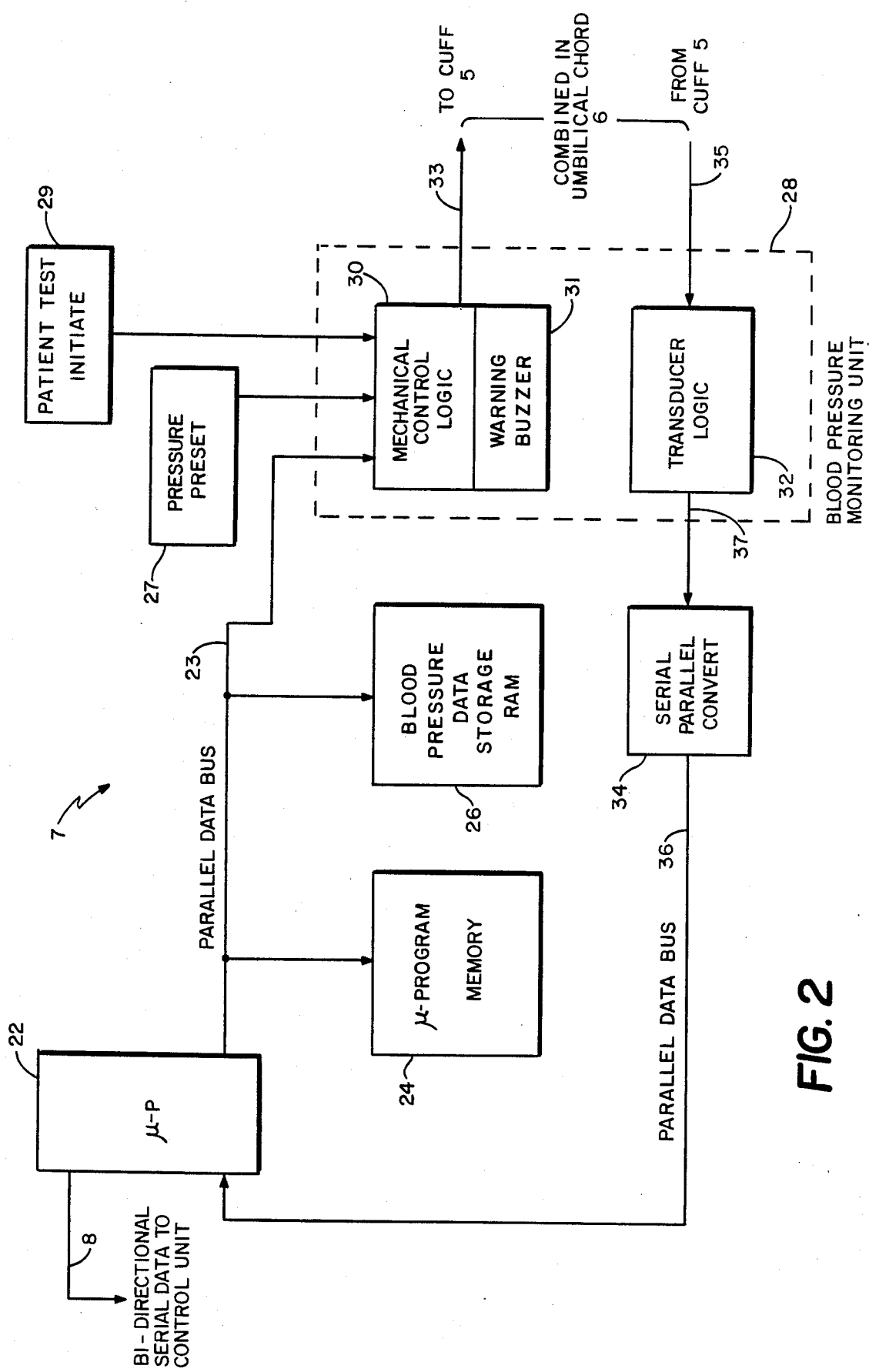
FIG. 2 is a more detailed block diagram of the patient unit.

FIG. 2 shows a more detailed block diagram of one preferred embodiment of patient unit 7. Patient unit 7 is controlled by microprocessor 22. Microprocessor 22 is electrically tied, via parallel data bus 23, to a microprogram memory 24. Microprocessor 22 accesses microprogram memory 24 and executes instructions stored therein. This method is well known in the art. In one preferred embodiment, microprogram memory 24 stores an algorithm for keeping real time. In that way, microprocessor 22 executes this algorithm and serves as a real time clock. Microprogram memory 24 also holds information which defines the blood pressure test regimen. In a preferred embodiment, that information consists of the interval of time between tests during daytime hours, the interval of time between tests during the night, and the pressure to which cuff 5 is to be inflated during the blood pressure test. Also, in one preferred embodiment, microprogram memory 24 contains an algorithm, executed by microprocessor 22, which detects unsuccessful blood pressure reading attempts due to inadequate pressure in cuff 5. After a preset number of failures due to inadequate cuff pressure, the microprocessor 22 automatically increases the cuff pressure and reinflates cuff 5 for another blood pressure reading.

Additionally, in one preferred embodiment, microprogram memory 24 contains an algorithm, executed by microprocessor 22, whereby microprocessor 22 can detect blood pressure readings which diverge significantly from previous blood pressure readings. Once such a blood pressure reading is detected, microprocessor 22 manipulates patient unit 7 such that, after a short period of time, another blood pressure reading is initiated. In this way, a new blood pressure reading is taken within a short time of when the significantly divergent blood pressure reading was taken and this new reading can substitute for the possibly erroneous, divergent reading.

Microprocessor 22 is also electrically connected via parallel data bus 23 to blood pressure storage RAM 26. Microprocessor 22 stores blood pressure reading information received from cuff 5 in the blood pressure storage RAM 26. The data is stored there so that it may be downloaded to control unit 9 at the appropriate time.

In this preferred embodiment, microprocessor 22 is also electrically connected via parallel data bus 23 to a blood pressure monitoring unit 28. The blood pressure monitoring unit 28 contains a patient test initiate button 29, mechanical control logic 30, and a warning buzzer 31. Microprocessor 22 executes instructions in the test regimen, which are contained in microprogram memory 24, thereby manipulating the mechanical control logic 30 so as to control cuff 5 during blood pressure tests. Cuff 5 is controlled via link 33 which is contained in umbilical cord 6. In one preferred embodiment, a small compressor, located in patient unit 7, is used to inflate cuff 5. The compressor is manipulated through mechanical control logic 30.

Microprocessor 22 also controls warning buzzer 31. The warning buzzer 31 is turned on and off according to the test regimen program stored in microprogram memory 24. Therefore, depending upon how microprogram memory 24 is programmed, warning buzzer 31 may be selectively masked. In this preferred embodiment, warning buzzer 31 is turned on a short time before a blood pressure reading is taken so that the patient may stop physical activity prior to the blood pressure reading. Because the patient is at rest, no cuff noises, which could be mistaken by the system to be Korotkoff pressure sounds, are introduced during the blood pressure reading. For this reason, the accuracy of the blood pressure reading is enhanced.

The patient may override microprocessor 22 and the test regimen stored in microprogram memory 24 by utilizing the pressure preset button 27 and the test initiate button 29. When test initiate button 29 is utilized, a blood pressure reading is taken and stored by microprocessor 22 in the blood pressure data storage RAM 26 regardless of the time intervals set up in the test regimen stored in microprogram memory 24. Similarly, pressure preset button 27 may be used to preset a cuff pressure regardless of the stored test regimen.

The blood pressure monitoring unit 28 also contains transducer logic 32. The transducer logic 32 operates on blood pressure reading signals received via link 35 from cuff 5. The result of this operation is a stream of electrical serial data signals 37 representing the blood pressure readings. This serial data is converted to parallel data, in the preferred embodiment, by manipulations undergone at a serial to parallel converter 34. Microprocessor 22 receives this data via parallel data bus 36. Microprocessor 22 then stores this data in the blood pressure storage RAM 26 via parallel data bus 23, as already described.

Also shown in FIG. 2 is the bi-directional serial data link 8 which links microprocessor 22 and, therefore, patient unit 7 to programmable control unit 9.

In FIG. 3, a more detailed block diagram of programmable control unit 9 is shown. In this preferred embodiment, control unit 9 is controlled by microprocessor 42. Microprocessor 42 contains resident storage RAM 44 which is used to store blood pressure data that is downloaded from patient unit 7, in particular from blood pressure storage RAM 26 via bi-directional serial data link 8.

Also shown in FIG. 3 is keypad input 46 which is used by the physician or nurse to provide information to microprocessor 42 via parallel data bus 48. Since control unit 9 is used to program microprogram memory 24 in patient unit 7, a physician or nurse inputs the test regimen for a particular patient unit 7 utilizing keypad input 46. Microprocessor 42 then transmits that information via bi-directional serial data link 8 to the particular patient unit 7 where it is stored in microprogram memory 24. Additionally, as will be described, keypad input 46 is used by a physician or nurse when transmitting information from control unit 9 to central processing computer 11. Keypad input 46 is also used to provide information to control unit 9 such as the patient's account number, telephone number, and social security number.

Microprocessor 42 is linked via parallel data bus 50 to microprogram memory 52. As in patient unit 7, microprocessor 42 accesses microprogram memory 52 and executes instructions stored therein. Microprocessor 42 is also linked by a parallel data bus 50 to LED display 54 and to dual tone multiple frequency (DTMF) interface 56. DTMF interface 56 is connected via electrical link 60 to speaker 62.

LED display 54 and speaker 62 combine to form an audio-visual means 64 which is used to prompt and instruct the physician or nurse on how to execute data transmission from control unit 9 to central processing computer 11. Microprocessor 42 reacts to information input by the nurse or physician from keypad input 46 and manipulates audio-visual means 64 to indicate to the physician or nurse whether they are proceeding in the proper manner.

DTMF interface 56 is connected via telephone lines 10 and phone switch 66 to central processing computer 11. In this preferred embodiment, the physician or nurse initiates the data transmission sequence by closing phone switch 66. This enables control unit 9 to be linked to central processing computer 11 via telephone line 10. The physician or nurse then inputs the telephone number of central processing computer 11 by keypad input 46. Microprocessor 42 transmits this telephone number via parallel data bus 50 to DTMF interface 56. DTMF interface 56 converts the electrical signals representing the telephone number to touch-tone signals to be sent over the telephone line 10 to central processing computer 11.

Once communication is established between control unit 9 and central processing computer 11 via telephone line 10, the blood pressure reading information, which was downloaded from patient unit 7 via bi-directional serial data link 8 and which was stored in resident storage RAM 44 on microprocessor 42, may be transmitted to central processing computer 11. The information is transmitted from microprocessor 42 via parallel data bus 50 through DTMF interface 56 over telephone line 10 to central processing computer 11.

In this embodiment, central processing computer 11 then returns a message over telephone line 10 to DTMF interface 56. The message either acknowledges that a successful data transmission has been completed, or that the data transmission has not been completed. DTMF interface 56 relays this message to the physician or nurse through electrical link 60 and speaker 62. Depending upon the message, the physician or nurse either disconnects the communication link between control unit 9 and central processing computer 11 by opening phone switch 66, or reinitiates the data transmission sequence.

Once the blood pressure reading information has been received by central processing computer 11, it is analyzed and compared with the broad base of data that central processing computer 11 has received from various other control units 9. Upon completion of analysis, central processing computer 11 generates medical reports based upon that analysis for the physicians who transmitted the data.

The reports that the physicians see are primarily error free. This is because of the methods used in patient unit 7 for detecting inadequate cuff pressure and automatically resetting it, for detecting blood pressure readings which diverge significantly from previous readings and automatically initiating a new blood pressure reading, and for alerting the patient, through a warning signal, that a blood pressure reading is about to be taken so that the patient may discontinue any physical activity which may cause an erroneous blood pressure reading. Using these methods eliminates most sources of error in blood pressure readings which are present in other ambulatory blood pressure monitoring systems.

The patient unit and control unit described in this invention are relatively inexpensive to manufacture. Since the primary function of the units is to take a substantially error free blood pressure reading and store it until such time as it is to be transmitted to a central processing computer, expensive and intricate algorithms and logic are unnecessary. The present invention, then, allows doctors an opportunity to utilize ambulatory blood pressure monitoring techniques without a significant capital investment.

Although the present invention has been described with reference to preferred embodiments, workers skilled in the art will recognize that changes may be made in form and detail without departing from the spirit and scope of the invention.

What is claimed is:

1. A system for acquiring, storing, transmitting, and processing blood pressure information, comprising:
   a plurality of patient units, each of which includes;
      an inflatable blood pressure measuring cuff,
      means for electronically manipulating the inflatable blood pressure measuring cuff to cause blood pressure readings to be taken from a patient,
      memory means for storing the pressure readings, and
      means for emitting a warning signal for alerting the patient at selectable times that the blood pressure reading will be taken so as to allow the patient an opportunity to discontinue physical activity thereby enhancing accuracy of the blood pressure reading;
   a plurality of programmable control units; each of which includes;
      means for programming patient units to select the selectable times,
      means for accessing the memory means within patient units allowing the blood pressure readings stored therein to be transmitted from the patient unit to the programmable control unit,
      means for communicating data over telephone lines, and
      means for storing the blood pressure readings received from patient units; and
   a central processing computer which includes;
      means for communicating data over telephone lines with the programmable control units,
      means for receiving and processing blood pressure readings from the programmable control units, and
      means for generating medical reports based on the blood pressure readings.

2. The system of claim 1 wherein each programmable control unit further includes:
   means for transmitting blood pressure readings, stored in the programmable control unit, over telephone lines to the central processing computer.

3. The system of claim 1 wherein each programmable control unit further includes:
   audio-visual means for prompting and instructing an operator as to the proper steps to enable the means for transmitting blood pressure readings to the central processing computer.

4. The system of claim 1 wherein each programmable control unit further includes:
   means for operator communication with the patient unit through the programmable control unit for programming a blood pressure test regimen.

5. The system of claim 1 wherein each programmable control unit further includes:
   means for transmitting blood pressure readings, stored in the programmable control unit, over telephone lines to the central processing computer;
   audio-visual means for prompting and instructing an operator as to the proper steps to enable the means for transmitting blood pressure readings to the central processing computer;
   means for operator communication with the patient unit through the programmable control unit for programming a blood pressure test regimen; and
   means for controlling the means for transmitting blood pressure readings, the audio-visual means, and the means for operator communication with the patient unit, through the programmable control unit.

6. A system for acquiring and storing blood pressure readings, the system comprising:
   an inflatable blood pressure measuring cuff means for electronically manipulating the inflatable blood pressure measuring cuff to cause blood pressure readings to be taken from a patient;
   memory means for storing the pressure readings; and
   means for emitting a warning signal for alerting the patient at selectable times that the blood pressure reading will be taken so as to allow the an opportunity to discontinue physical activity thereby enhancing accuracy of the blood pressure reading.

7. The system of claim 6 and further including:
   means for selectively masking the warning signal, based on the time kept by the means for keeping real time, for allowing the warning signal to be masked at preselected times of the day and night.

* * * * *

UNITED STATES PATENT AND TRADEMARK OFFICE
CERTIFICATE OF CORRECTION

PATENT NO. : 4,830,018

DATED : May 16, 1989

INVENTOR(S) : James E. Treatch

It is certified that error appears in the above-identified patent and that said Letters Patent is hereby corrected as shown below:

Column 5, line 51, delete ";", insert --,--.

Column 6, lines 46-49, delete "an inflatable blood pressure measuring cuff means for electronically manipulating the inflatable blood pressure measuring cuff to cause blood pressure readings to be taken from a patient" and insert the following:

--an inflatable blood pressure measuring cuff;

means for electronically manipulating the inflatable blood pressure measuring cuff to cause blood pressure readings to be taken from a patient--

Column 6, line 53, after "the", insert --patient--

Signed and Sealed this

Thirtieth Day of January, 1990

*Attest:*

JEFFREY M. SAMUELS

*Attesting Officer*  *Acting Commissioner of Patents and Trademarks*